United States Patent [19]

Welsh

[11] Patent Number: 5,557,028
[45] Date of Patent: Sep. 17, 1996

[54] ALKYLATION REACTIONS

[76] Inventor: Stanely M. Welsh, 2813 E. Fox Chase Cir., Doylestown, Pa. 18901

[21] Appl. No.: 414,709

[22] Filed: Mar. 31, 1995

[51] Int. Cl.$^6$ .................................................. C07C 2/62
[52] U.S. Cl. ........................... 585/724; 585/723; 585/732
[58] Field of Search ..................... 585/732, 723, 585/724

[56] References Cited

U.S. PATENT DOCUMENTS 3,773,843  11/1973  Schmerling .............................. 585/732
3,855,325  12/1974  Schmerling .............................. 585/732

*Primary Examiner*—Asok Pal
*Attorney, Agent, or Firm*—Stanley M. Welsh

[57] ABSTRACT

Improved acid catalyzed alkylation reactions occur for the addition of a hydrocarbyl reactant to an alkene, by the optimized addition of an oxidizing agent, such as a peroxide, molecular oxygen, ozone, peracid, and one or more of the peroxide, molecular oxygen, ozone, or peracid mixed with at least one material selected from the group consisting of the hydrocarbyl reactant, and the alkene. The hydrocarbyl species contains at least one tertiary carbon atom attached to hydrogen, such as isobutane. The alkene is preferably 1- or 2-butene. Suitable peroxides are found in the group consisting of: tert-butyl peroxyneopentanoate $((CH_3)_3C-O-OCO-C(CH_3)_3)$; acetyl peroxide $(CH_3CO-O-O-COCH_3)$; di-tert-butyl peroxide $((CH_3)_3C-O-O-C(CH_3)_3)$; hydrogen peroxide $(H_2O_2)$ and peracids of carboxylic acid having up to 10 carbon atoms, and a general chemical formula $C_nH_{2n}O_3$, where n has values in the range 2–10. Examples of peracids having the general chemical formula are: perisopentanoic acid: $(CH_3)_3CCO-O_2H$ corresponding to $C_5H_{10}O_3$); peracetic acid: $CH_3CO-O_2H$ corresponding to $C_2H_4O_3$. A non-acid catalyzed alkylation alternative is also disclosed.

24 Claims, No Drawings

5,557,028

ALKYLATION REACTIONS

Disclosure Document having No. 373303 received by Patent Office Mail Room on Mar. 29, 1995 contains material that substantially disclosed the material found in this application.

BACKGROUND OF THE INVENTION

1. Field of the Invention

This invention relates to the preparation of gasoline blending additives used to increase a transportation fuel's octane. More specifically, this invention relates to the use of strong acids, like sulfuric or hydrofluoric acids, to catalyze the addition of tertiary carbon atoms such as found in t-butane to an alkene such as found in 2-butane.

2. Description of the Prior Art

Many studies are reported on an acid catalyzed alkylation of alkenes by an alkane containing a tertiary carbon atom bound to hydrogen. In all of these studies, a hydride ion transfer from the tertiary carbon to an alkane-alkene intermediate is proposed. An example of these reactions is:

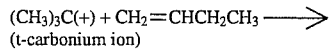
(t-carbonium ion)

(CH$_3$)$_3$CCH$_2$C(+)HCH$_2$CH$_3$
(alkane-alkene intermediate)

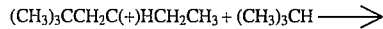

(CH$_3$)$_3$CCH$_2$CH$_2$CH$_2$CH$_3$ + (CH$_3$)$_3$C(+)
(alkylation product)

The production of a new tertiary carbonium ion that adds to another alkene allegedly drives the reaction forward as alkylation products such as 2,2-dimethyl hexane and acid catalyzed rearrangements thereof are removed by separation from the reaction medium. To avoid side reactions, such as alkenes reacting with the alkane-alkene intermediate or themselves, excess alkane over alkene is used, often on the order of 20:1 weight percent alkane:alkene. The reaction temperature is usually kept low in the range of 10°–20° C.

Examples of such literature references are briefly cited below.

Kirk-Othmer Encyclopedia of Chemical Technology (Fourth Edition, Vol. 2, page 87) refers to three studies of strong acid catalysis of tertiary carbon addition to an alkene. These studies were: L. Schmerling, Journal of the American Chemical Society, Vol. 68, 275 (1946); F. G. Ciapetta, Industrial Engineering Chemistry, Vol. 37, 1210 (1945); and J. E. Hoffman & A. J. Schriescheim, Journal of the American Chemical Society, Vol. 84, 953–961 (1962).

J. W. Otvos, D. P. Stevenson, C. D. Wagner, and O. Beeck reported in the Journal of the American Chemical Society, Vol. 73, 5741 (1951) in an article entitled, "The Behavior of Isobutane in Concentrated Sulfuric Acid", that L. Schmerling's interpretation of the alkylation of alkenes by isobutane was essentially correct. They found: 1. no skeletal isomerization of either n-butane or isobutane; 2. there was no hydrogen exchange between molecules of n-butane (intermolecular) or between primary and secondary carbon atoms of a single n-butane (intramolecularly); 3. the tertiary hydrogen of t-butane does not exchange with acid protons of sulfuric acid, but the primary hydrogens do; 4. the tertiary hydrogens can be made to exchange by the addition of 0.1% of either isobutylene or 2-butane; 5. the apparent exchange rate between tertiary deuterated C$^{13}$ labeled and C$^{12}$ unlabeled isobutane revealed the rate of loss of tertiary D from the labeled isobutane matched the rate of increase in the amount of D in the unlabeled isobutane.

These results provided the basis for proposing the following reaction scheme:

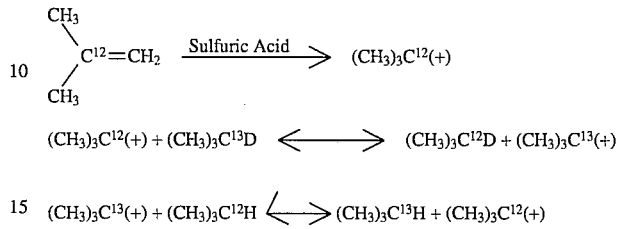

These experimental observations and interpretations have lead to the universally accepted conclusion that scrambling of tertiary deuterium atoms of isobutane (also known as 2-methylpropane, tart-butane, isobutane, i- or t-butane) was due to a hydride ion transfer of a tertiary hydrogen of isobutane to a secondary or tertiary carbonium ion produced indirectly by protonation of an alkene or from an addition product intermediate that results from isobutylene adding to itself due to an acid catalysis.

In summary, the sulfuric acid catalyzed addition of isobutane to an olefin, such as propylene or butene, was believed to require a hydride ion transfer of the tertiary hydrogen of isobutane to an alkane-alkene intermediate containing a carbonium ion to produce another tertiary carbonium ion that would propagate the reaction by adding to another olefin.

Provided that the alkane, such as t-butane, is in large enough excess over the alkene, the formation of polymers or polyadducts can be suppressed and minimized.

In reaching this invention, the inventor began with the conviction that the above proposed mechanism could not be right. The reasoning was as follows. It is unlikely that simple thermal energy at temperatures under 50° C. will be sufficient to polarize the C—H bond in tertiary butane merely by the approach of a secondary or even a tertiary carbonium ion so that the transition state:

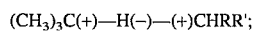

where R and R' are any alkyl group such as found in a typical alkylation adduct, is reached. As the transition state is approached, the hydrogen in the C—H bond allegedly becomes more and more negative. Since a hydrogen atom in a chemical bond with carbon is simply a very small proton nucleus surrounded by electrons that are primarily under the influence of carbon molecular orbitals, a more accurate picture of the hydrogen to carbon bond is a hydrogen nucleus imbedded in the electron cloud that surrounds the carbon atom.

Utility and Objects of the Invention

In light of the importance of producing blending components to increase the octane of transportation fuels such as diesel and gasoline, this invention discloses in part and in some of its embodiments ways to vary process variables for a conventional acid catalyzed alkylation of a hydrocarbyl specie containing at least one tertiary carbon to an alkene that improves yields and process performance, such as reducing the amount of an organic sludge and other environmentally undesirable side reactions that would otherwise be produced.

SUMMARY OF THE INVENTION

General Statement of the Invention

Opportunities to run a conventional strong acid catalyzed alkylation reaction in surprising and unexpected ways become evident to one, once one realizes that there is an alternative mechanism involved. Such an alternative mechanism must account for the products produced and explain how a tertiary hydrogen of a hydrocarbyl specie like isobutane is transferred to a reaction product intermediate formed during the acid catalyzed addition of the hydrocarbyl specie to an olefin.

I believe the actual mechanism involves a transfer of a hydrogen atom rather than a transfer of a hydride ion. Additional evidence justifying this alternative mechanism is available. However, this information has been overlooked until now for almost 50 years! The evidence is as follows.

A small amount of oxygen is almost inevitably entrained in any alkene. This fact is clear from the anti-Markovnikov addition of hydrobromic acid to 1-pentene. HBr adds to 1-pentene to yield 1-bromopentane and 2-bromopentane in a ratio of Markovnikov (2-bromopentane) to anti-Markovnikov (1-bromopentane) that varied depending upon the amount of exposure to air. These results were explained in terms of a free radical catalyzed addition of HBr and an acid catalyzed addition of HBr to the 1-pentene. In a free radical catalyzed reaction, a bromide radical adds to the primary carbon, because a secondary carbon radical is more stable than a primary carbon radical. In an acid catalyzed reaction, a proton adds to the primary carbon of 1-pentene, because a secondary carbonium ion is more stable than a primary carbonium ion. Hence it is clear that either a radical or a positive charge is most favored on a tertiary carbon atom, followed by a secondary carbon atom, followed by the least favored, a primary carbon atom. The free radical addition of HBr is suppressed by the presence of hydroquinone or other free radical scavengers.

These HBr additions can be visualized as follows:

With Acid Catalyzed Addition of Br(−):

$$H(+)+CH_3(CH_2)_3CH=CH_2 \rightarrow CH_3(CH_2)_3CH(+)-CH_2H$$

$$CH_3(CH_2)_3CH(+)-CH_2H+HBr \rightarrow CH_3(CH_2)_3CHBr-CH_2H+H(+)$$

With Free Radical Catalyzed Addition of Br·:

$$Br·+CH_3(CH_2)_3CH=CH_2 \rightarrow CH_3(CH_2)_3CH(·)-CH_2Br$$

$$CH_3(CH_2)_3CH(·)-CH_2Br+HBr \rightarrow CH_3(CH_2)_3CH_2-CH_2Br+Br·.$$

The important point being that a free radical-like species is generated in the presence of oxygen and an acid. This then provides a consistent alternative explanation of what caused the rapid transfer of hydrogen between labelled tertiary butanes when isobutylene was added. The isobutylene introduced a small amount of oxygen which turned the tertiary carbon into a free radical. Transfer of hydrogen atoms, neutral free radicals, is a more plausible way to explain the results, since the energy required for such an exchange is considerably lower than that which would be required for a hydride ion transfer under similar circumstances of temperature and pressure.

This then explains how simply bubbling a radical generating agent like oxygen with or without an alkene sufficiently near an interphase between a strongly acidic phase and an organic phase consisting of hydrocarbyl species that contain a tertiary carbon bonded to hydrogen will cause free radicals to be generated in the organic phase. The alkene is preferably diluted with the hydrocarbyl species to reduce acid catalyzed coupling of alkenes. The organic phase preferably includes, but is not required to, a hydrocarbyl material which can dissolve the hydrocarbyl specie and alkene and which is substantially insoluble in the strongly acidic phase.

The reactions are believed to proceed in the following way:

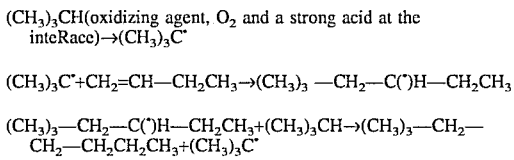

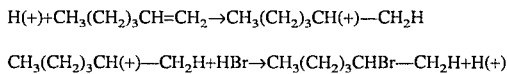

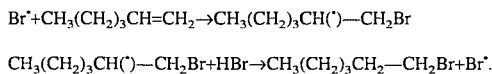

The chemical significance or consequence of an abstraction of any one of the 9 possible primary hydrogens of t-butane instead of the single tertiary hydrogen initially or otherwise will quickly be lost as a result of equilibrating exchanges among t-butanes, because the stability of a tertiary carbon radical is so much greater than that of a primary carbon radical.

Once the hydrocarbyl specie that contains a tertiary carbon bonded to a hydrogen atom, such as tertiary butane, becomes a free radical at or very near the interface where the organic phase and the acid phase meet, rapid migration of that free radical-like species into the organic phase will occur. The migration of the free radical-like species merely requires a series of hydrogen atom jumps between t-butane molecules. The migration is very rapid, much like the apparent migration of a solvated proton through an aqueous phase. The destruction of radical species including any radical generating agent such as the following oxidizing agents: ozone or a peroxide that one might expect from the presence of a strong acid is at least in part overcome due to the rapid migration of the free radical of the hydrocarbyl specie away from the interface and into the organic hydrocarbyl reaction phase. Also undesirable side reaction due to radical fragments, such as may be produced by the interaction of ozone or oxygen with radical intermediates, are suppressed.

Protonation of alkenes introduced into the organic hydrocarbyl reaction phase is preferably avoided in order to minimize side reactions such as an acid catalyzed addition of one alkene with another or formation of an organic sludge in general. One way to minimize such protonation is to add alkenes only at a distance away from the acid/organic interface, so that diffusion or other forms of migration to the interface by an alkene will not occur significantly in contrast to reaction with a hydrocarbyl specie that has become a tertiary carbon free radical. In addition, it would be preferable to add fresh hydrocarbyl species between the point of addition of additional alkenes to the organic phase and the acid/organic interface, so that there is a net flow of material away from the interface into other portions of the hydrocarbyl reaction phase, which further lessens the tendency of an alkene to migrate to the interface and become protonated.

Since contact between alkenes and the protonating tendency of the acid phase is minimized a much cleaner reaction process design is possible without the requirement for high energy mixing of the acid and organic phases to form emulsions or dispersions.

For purposes of this specification and claims, the term "hydrocarbyl" when used to identify a material, specie, medium, intermediate, blending component, or phase shall mean a material, specie, medium, intermediate, blending component, or phase that consists essentially of carbon and hydrogen atoms with no more than 5% by weight of other atoms such as oxygen, halide, nitrogen, or sulfur. "Halide" includes one or more atoms of fluorine, chlorine, bromine, or iodine. Preferably, there will be less than 1% by weight, and ideally substantially none of such other atoms present in the hydrocarbyl.

The term "near" an interface between phases is a relative term which will depend upon the amount of mixing that is occurring at the interface and the stability of the radical generating agent to strong acid. For example, if the addition of molecular oxygen at the interface causes a great deal of mixing between the two, then the distance from the interface preferably will be larger to take into account a greater tendency of the acid phase to migrate into the hydrocarbyl organic phase. However, if the radical generating agent is very unstable, then addition near the interface will preferably be into the organic phase, or preferably with a diluent when added into the acid phase. Any hydrocarbyl free radical generated preferably is given an opportunity to migrate into the organic phase without being destroyed by the presence of any strong acid. Other materials such as an alkene, having from 3 to 10 carbon atoms, can be added "near" the interface to encourage reaction between the alkene and a hydrocarbyl free radical, having from 4 to 10 carbon atoms, wherein the radical is on a tertiary carbon.

"Encouraging" in the sense of facilitating the reaction of a free radical addition to an alkene means adopting one or more of the following strategies: controlling amount present of an oxidizing agent such as oxygen and maintaining reactants at a temperature, wherein each are individually optimized to achieve at least 80% of the maximum yield otherwise achievable by merely varying temperature or the amount of the oxidizing agent, while keeping all other process variables substantially constant, and preferably at least 90% of said maximum yield; maintaining a sufficient excess of alkane over alkene in the hydrocarbyl reaction phase so as to reduce and preferably eliminate unwanted side reactions such as two or more alkenes coupling to form species having more than 8–15 carbon atoms; adding alkane or recycling material (as for example a reaction phase stream) "near" the interface so as to promote a net flow of reactants away from the interface and thereby inhibit diffusion of alkenes to the interface where they might become protonated; separating products from the hydrocarbyl reaction phase to form a reaction phase stream and a product stream and recycling back at least a portion of the reaction phase stream into the hydrocarbyl reaction phase "near" the interface. The precise location of the recycle stream is not critical, but it can be used to reduce side reactions and promote free radicals, as for example when used as a diluent for the radical generating agent. The amount of oxygen present will generally be at least 0.01%, more preferably at least 0.05% by weight, and still more preferably at least 0.5% by weight, as based upon the weight of alkene present, and generally in the range of 0.05 to 2% by weight of the weight of alkene present.

"Sufficient excess" in general will depend upon the particular reactant and reaction conditions. A "sufficient excess" of alkane over alkene will inhibit side reactions to less than 5% by weight, and preferably less than 1% by weight, and still more preferably less than 0.1% by weight and ideally less than 0.01% by weight as based upon product yields of desired products such as $C_8$ hydrocarbons produced.

"Substantially optimizing a reaction process or its yields by control of a selected process variable such as temperature or amount of an oxidizing agent or free radical generating agent that produces directly or indirectly a t-butyl radical on its tertiary carbon" means throughout this specification and claims to control said selected process variable to a value wherein carrying out the process keeping all other process variables substantially constant, results in a yield of useful products equal to at least 80% and still more preferably at least 90% of the maximum achievable yield obtainable by optimizing said selected process variable, while keeping all other variables substantially constant.

Addition of molecular oxygen so as to pass from the strongly acidic phase into the hydrocarbyl reaction phase is preferably carried out so as to maximize the amount of tertiary carbon atom free radicals produced in the hydrocarbyl reaction phase. It is to be noted that it should be possible to produce some 2,2,3,3-tetramethylbutane, a specie which provides the largest increase in octane of all known hydrocarbyl blending components. Temperature control is necessary to optimize yield of 2,2,3,3-tetramethylbutane and lessen formation of disproportionate products like isobutane and isobutylene.

Unreacted molecular oxygen should be removed from the system and preferably recycled. A build up of molecular oxygen in the acid phase is undesirable, because it often leads to the formation of water. Any significant amounts of water present will cause sulfuric acid or hydrofluoric acid to become intolerably corrosive with much more severe wear on production equipment than would otherwise occur simply from the use of pure sulfuric acid or hydrofluoric acid. To maintain the acid phase in a substantially anhydrous condition, the addition of fuming sulfuric acid to the sulfuric acid from time to time is recommended. Fuming sulfuric acid contains $SO_3$ which reacts with water to form sulfuric acid. Also during regeneration by methods well known in the art of either sulfuric or hydrofluoric acid to remove organic components, water removal by methods also well known in the art is recommended. Separation of such molecular oxygen can be carried out through a sudden drop in pressure of the hydrocarbyl reaction phase or decantation in a gas liquid separation vessel or both carried out alternately or simultaneously. Separation of products from the hydrocarbyl reaction phase can be carried out by distillation and other methods well known in the relevant art.

DETAILED DESCRIPTION OF THE INVENTION AND PREFERRED EMBODIMENT

In an otherwise conventional strong acid catalyzed reaction of isobutane and an alkene, one controls the amount of molecular oxygen or other agent that leads to the formation of tertiary carbon free radicals. Several places are available for such addition. To understand where they are, a schematic overview of a conventional acid catalyzed alkylation unit is helpful.

Modern Petroleum Technology 4th Edition, edited by G. D. Hobson in collaboration with W. Pohl, and published by Applied Science Publishers LTD discusses a sulfuric acid alkylation on pages 348 to 350. The process involves:

contacting in a first reaction zone, an isobutane and an olefin feed with sulfuric acid;

separating a predominantly organic stream from said first zone;

separating a predominantly acid stream from said first zone;

treating said organic stream to substantially remove all acidic components, and then separating said organic stream having few, if any, acid components into the following organic components: an n-butane stream, a recycle isobutane stream, and two or more alkylate streams depending upon their molecular weight;

treating a portion of said predominantly acid stream to remove organic materials and recycling the remainder back to the first reaction zone;

replacing with fresh sulfuric acid a portion of spent sulfuric acid from the first zone which is treated and then discarded.

The feed streams to the reactor are: fresh and recycled isobutane; and fresh and recycled acid. The streams from the reactor are: a predominantly organic stream with entrained acidic components and a spent acid stream. The temperature of the reactor is kept at a temperature in the range 4° to 13° C. for optimal results. The alkylation reaction is quite exothermic and the temperature is preferably kept below 20° C. for optimal results. The more isobutane as measured in liquid hourly space velocity the generally higher is the octane of the alkylate product streams separated.

The predominantly organic stream is often separated from most of the acidic components by a simple process of settling followed by decantation to form a predominantly organic stream which is then treated in a treating vessel or zone to remove entrained acidic materials. Caustic and water washing, or bauxite or hot water washing are all possible ways of treating the predominantly organic stream to remove acidic components and produce a debutanizer feed comprising substantially only organic materials.

The debutanizer feed is separated into an n-butane stream, a recycle isobutane stream, and two or more alkylate streams depending upon their molecular weight and corresponding boiling points. The alkylate streams correspond to the reaction products that are acid catalyzed adducts of the isobutane and olefin feeds.

Spent acid is separated by decantation from the bottom of the reaction vessel. The spent acid is either discarded or regenerated to remove any entrained organic material and recycled back into the reactor.

An alternative reactor design to that given above is disclosed in Petroleum Refining Technology and Economics Second Edition, edited by James H. Gary and Glenn E. Handwerk, and published by Marcel Dekker, Inc of New York and Basel on pages 169 and 170. The acid contacting vessel provides for incremental addition of the olefin to a series of zones. The acid contacting is carried out in as many as five separate zones, with effluent from each prior zone being transferred to an immediately subsequent zone. Since the olefin is introduced in incremental amounts, the process could be modified in accordance with one embodiment of this invention to control and therefore adjust the molecular oxygen present in the olefin to optimize the yields that are achieved. Petroleum Refining Technology and Economics Second Edition, edited by James H. Gary and Glenn E. Handwerk, and published by Marcel Dekker, Inc of New York and Basel on page 165 discloses a hydrofluoric acid process consisting of:

contacting a dehydrated isobutane stream and a dehydrated olefin stream with hydrofluoric acid in a contactor at sufficient pressure to maintain all components in a liquid phase to provide a reaction mixture;

allowing in a settling vessel, the reaction mixture to separate into two liquid layers: an acid layer, which being more dense becomes a bottom layer, and an organic layer, which being less dense, becomes a top layer;

withdrawing a small slip-stream of the acid layer and separating it by distillation into an overhead product of substantially pure hydrofluoric acid that is recycled into the contactor after appropriate cooling; dissolved water in the form of an HF water azeotrope which is often neutralized with lime or caustic and discarded; and polymerized hydrocarbons, which are often used for fuel.

decanting in the settling vessel at least a portion of the organic layer from the top layer and separating by distillation in one or more columns into propane, isobutane, normal butane, and an alkylate product along with a small amount of hydrofluoric acid; (Propane and normal propane products streams are often passed through caustic treaters to remove trace impurities and hydrofluoric acid.)

cooling the acid phase to remove at least a portion of any heat of reaction and maintain the acid hydrocarbon mixture at no more than 30° C., and generally in the range 70°–80° F. (21°–27° C.).

In general, in any acid catalyzed alkylation, there often is a location upstream of a typical mixing step that produces an emulsion of acid, alkane, and alkene, where the alkane may be added to the acid prior to the addition of the alkene. However, more typically, the alkane and alkene are mixed together with an excess of alkane to alkene and then together are made into an emulsion or dispersion with the acid. In general, regardless of location for addition of alkane and/or alkene, the process conditions that control product yield and product distribution are: weight hourly space velocity which relates contact time between an organic phase and an acid phase in units of weight of organic phase to volume of acid phase per hour; ratio of alkane to alkene which is preferably at least 1.5 moles of alkane to each mole of alkene, preferably at least 5 moles of alkane for each mole of alkene and still more preferably at least 10 moles of alkane for each mole of alkene and generally the ratio in moles of alkane to alkene is in the range of about 1.5:1 to 20:1; temperature which is preferably kept under 40° C. is generally in the range of about 0° to 30° C.; pressure at a value sufficient to maintain volatile components of alkanes and alkenes in solution and as liquids; and now recognized for the first time as explained in this specification, the amount of oxidizing agent, such as for example, molecular oxygen present.

Still another way to run the reaction in accordance with this invention is to expose the alkene to oxygen prior to mixing with the alkane. Then instead of forming an acid emulsion or dispersion, which is still an option, simply pass the mixture as preferably finely dispersed bubbles or droplets through at least a portion of the acid phase of either sulfuric or hydrofluoric acid. Additional alkenes are preferably added with or without additional alkanes to the organic phase, which is intended to be present, if not already formed, after passage through at least a portion of the acid phase. A key to reaction performance of this embodiment is to control the amount of molecular oxygen dissolved in the alkene and temperature of reactants, preferably below 20° C., and more preferably below 10° C. Preferably the values for temperature and amount of oxygen are those which optimize yields, all other factors remaining substantially constant, to at least 80% and still more preferably to at least 90% of maximum yield otherwise achievable.

Modifications

Specific compositions, methods, or embodiments discussed in this specification are intended to be only illustrative of the claimed invention. Variations of any of these that would be readily apparent to a person of skill in the art based upon the teachings of this specification and the knowledge and skill of a person of ordinary skill in the relevant art are intended to be within the scope of the disclosed invention.

Suitable radical generating agents, which are usually also oxidizing agents can be usefully added or produced in-situ. Examples of these agents include the following: tert-butyl peroxyneopentanoate (($CH_3$)$_3$C—O—OCO—C($CH_3$)$_3$); acetyl peroxide ($CH_3$CO—O—O—CO$CH_3$); di-tert-butyl peroxide (($CH_3$)$_3$C—O—O—C($CH_3$)$_3$); hydrogen peroxide ($H_2O_2$) and peracids of carboxylic acid having up to 10 carbon atoms, and a general chemical formula $C_nH_{2n}O_3$, where n has integer values in the range 2–10. Examples of peracids having the general chemical formula are: perisopentanoic acid: ($CH_3$)$_3$CCOO—$O_2$H corresponding to $C_5H_{10}O_2$); peracetic acid: $CH_3$CO—$O_2$H corresponding to $C_2H_4O_3$.

For still another example, the first phase is not a strongly acidic phase such as substantially pure sulfuric acid or hydrofluoric acid. Instead, the first phase is an anode electrolyte material, which is selected so as to be capable of supporting an anodic current to remove an electron from a carboxylate group of an organic acid in accordance with a Kolbe-like reaction to produce a hydrocarbyl free radical. However, the second phase, in which the tertiary carbon radical is used to react with itself or an alkene, is substantially unchanged, except to optionally make it more capable of dissolving at least a portion of an anodic electrolyte material or phase. A cathodic electrolyte solution or phase is kept separate from the first and second phases of this example, except to the extent of supporting current through the cathode and anode. Biradical coupling reactions are substantially prevented: either by using as at least a portion of the organic acid feed, highly branched organic acids such as isopentanoic acid; or by sweeping the electrode's surface at a sufficient rate with at least a portion of the second phase, or any of its components, such as a stream of hydrocarbyl materials which contain a tertiary carbon bonded to a hydrogen. This hydrogen bonded to the tertiary carbon exchanges with the organic free radical produced near the anode's surface.

In a cell not unlike one appropriate for the instant invention with the exception of electrode materials, an organic electrochemical reaction has been reported, which caused two molecules of acrylonitrile to be reduced by transfer of two electrons from a cathode. These negative acrylonitrile radicals couple, before accepting any protons from water. The coupling of the two radicals to form a bond destroys the free radical character of these materials. A doubly negative reaction intermediate results. This intermediate accepts two protons from water to yield adiponitrile. A cathodic electrolyte solution or phase is kept separate from the first and second phases of this example, except to the extent of supporting current through the cathode and anode.

By contrast the organic electrochemical reaction of this invention takes place at the anode. The anodic and cathodic solutions or phases are kept substantially separate in the sense described above. The anodic electrolyte solution or first phase is compatible with the second phase in that it is at least in part soluble in one or more components in the second phase of this invention. The cathodic solution can be any material which will support a current at appropriate current levels in conjunction with that current supported by the anodic electrolyte phase or solution. Details as to the best procedure for carrying out a Kolbe-like reaction are disclosed in "Advances in Organic Chemistry: Methods and Results", Published by Interscience Publishers, Vol. 1, beginning on page 5 (QD 251.A36). For appropriate cell designs that utilize electrolytes in an organic or aqueous phase that flow passed relevant electrodes in conjunction with the optional use of polyelectrolytes such as Nation, see Techniques of Electroorganic Synthesis (QD 61.T4) Edited by N. L. Weinberg, and published by John Wiley and Sons, volume V, parts 1 and 2. Cell designs appropriate for commercial applications are specifically discussed along with the parameters of aqueous and non-aqueous solvents suitable for particular current and voltage ranges.

Nation is the trademark name owned by DuPont for a commercially available perfluorinated cation exchange polymer membrane. An example of its structure is believed to be:

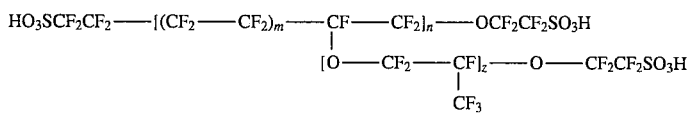

where n=about 1000; Z=1,2, or 3; and m=5–13.5, with an ion exchange capacity of 1.05 meq/gram to 0.55 meq/gram.

Reference to all or any portion of any document made anywhere in the specification is intended to result in all such documents, be they patents, or any other printed publications, including documents referenced in such documents, being expressly incorporated herein by reference in their entirety.

Each expressly identified numerical range within this specification is intended to incorporate by reference and therefore expressly include and provide express support as required by 35 U.S.C. 112 for each and every numerical member of each such range including each and every possible range within each such expressly identified numerical range. For example, a numerical range of 1 to 100, is intended to provide express support for any range within such numerical range, such as 3 to 28, or 72 to 94 etc. and also to provide express support for any specific numerical member of the range 1 to 100, such as 25, or 63 etc.

What is claimed is:

1. A process for producing at least one hydrocarbyl blending component to improve gasoline octane comprising:

near an interface between two phases comprising a first phase and a second phase, generating a free radical on a tertiary carbon atom of a hydrocarbyl reactant containing said tertiary carbon atom; wherein said first phase and said second phases are characterized in that they are at a temperature under 40° C. and substantially insoluble in one another, wherein said first phase comprises a material selected from a group consisting of sulfuric acid and hydrofluoric acid, and wherein said second phase comprises a hydrocarbyl reaction medium comprising one or more materials selected from the group consisting of said hydrocarbyl reactant and a hydrocarbyl solvent for said hydrocarbyl reactant;

encouraging reaction of said free radical with an alkene within said second phase by controlling amount of at least one oxidizing agent to optimize yield of said at least one hydrocarbyl blending component.

2. The process of claim 1, wherein said at least one oxidizing agent is selected from a group consisting of a peroxide, oxygen, and ozone in an amount controlled to optimize yield of said at least one hydrocarbyl blending component.

3. The process of claim 2, wherein said at least one oxidizing agent is a peroxide.

4. The process of claim 2, wherein said at least one oxidizing agent is oxygen.

5. The process of claim 2, wherein said at least one oxidizing agent is ozone.

6. The process of claim 2, wherein said at least one oxidizing agent is a combination of oxygen and ozone.

7. The process of claim 3, wherein said peroxide is selected from the group of peroxides consisting of: periacids having a general chemical formula: $C_nH_{2n}O_3$, where n=an integer of from 2–10; tert-butyl peroxyneopentanoate; acetyl peroxide; di-tert-butyl peroxide; and hydrogen peroxide.

8. The improved process of claim 2, wherein to "substantially optimize" means to maintain that amount of said oxidizing agent which promotes a yield which is at least 80% of maximum reachable yield through control of said amount of said agent while all other factors are held substantially constant.

9. The improved process of claim 8, wherein said yield is at least 90% of said maximum reachable yield.

10. The process of claim 2, wherein said oxidizing agent is diluted with at least one material selected from a group consisting of said hydrocarbyl reactant, said hydrocarbyl reaction medium, said hydrocarbyl blending component, and said alkene.

11. In a process that uses sulfuric acid or hydrofluoric acid at under 40° C. to react an alkene with a hydrocarbyl reactant containing a tertiary carbon bonded to hydrogen, the improvement which comprises producing a free radical on said tertiary carbon by contacting said hydrocarbyl reactant with an oxidizing agent whose amount is controlled to optimize said process.

12. The improved process of claim 11, wherein to optimize said alkylation process, amount of said oxidizing agent is controlled so that said yield which is achieved is at least 80% of maximum reachable yield through optimal control of amount of said agent.

13. The improved process of claim 12, wherein said yield which is achieved is at least 90% of said maximum reachable yield.

14. The improved process of claim 11, wherein said oxidizing agent is selected from a group consisting of a peroxide, molecular oxygen, ozone, and one or more of said peroxide, molecular oxygen and ozone mixed with at least one material selected from a group consisting of said hydrocarbyl reactant, and said alkene.

15. The improved process of claim 14, wherein said oxidizing agent is a peroxide.

16. The improved process of claim 15, wherein said peroxide is selected from the group of peroxides consisting of: a peracid having a general chemical formula: $C_nH_{2n+1}CO—O_2H$, where n=an integer value of from 2–10; tert-butyl peroxyneopentanoate; acetyl peroxide; di-tert-butyl peroxide; and hydrogen peroxide.

17. The improved process of claim 14, wherein said oxidizing agent is molecular oxygen.

18. The improved process of claim 14, wherein said oxidizing agent is a combination of molecular oxygen and ozone.

19. The improved process of claim 11, wherein said alkylation process involves a step of forming a mixture comprising said alkene, said hydrocarbyl reactant and an acid selected from a group consisting of sulfuric acid and hydrofluoric acid, and wherein said oxidizing agent is added to said mixture.

20. The improved process of claim 19, wherein said agent is added to at least one of a material selected from the group consisting of said alkene and said acid prior to forming said mixture.

21. In a process for adding a hydrocarbyl specie to an alkene, wherein said hydrocarbyl specie contains at least one tertiary carbon atom bonded to hydrogen and wherein contact with a strong acid selected from a group consisting of sulfuric acid and hydrofluoric acid is used to form a gasoline blending component which improves octane, the improvement which comprises prior to contacting a feed comprising said hydrocarbyl specie and said alkene with said acid, controlling amount of oxygen within said feed to optimize yield for said gasoline blending component.

22. The improved process of claim 21, wherein to substantially optimize said yield, amount of said oxygen is controlled so that said yield for said gasoline blending component is at least 80% of maximum yield reachable for said gasoline blending component through optimal control of amount of said oxygen.

23. The process of claim 2, wherein said acid is sulfuric acid.

24. The process of claim 2, wherein said acid is hydrofluoric acid.

* * * * *